(12) United States Patent (10) Patent No.: US 8,180,421 B2
Phillips et al. (45) Date of Patent: May 15, 2012

(54) RESONANCE ENERGY TRANSFER BASED DETECTION OF NOSOCOMIAL INFECTION

(75) Inventors: Erica M. Phillips, Woodstock, GA (US);
Richard Hantke, Chicago, IL (US);
Daniel Baird, Woodstock, GA (US);
Mike Rainone, Palestine, TX (US);
Thomas Edward Plowman, Cary, NC (US); Talbot Presley, Palestine, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1097 days.

(21) Appl. No.: 11/954,848

(22) Filed: Dec. 12, 2007

(65) Prior Publication Data

US 2009/0156942 A1 Jun. 18, 2009

(51) Int. Cl.
*A61B 5/1455* (2006.01)
*G01N 21/00* (2006.01)
(52) U.S. Cl. ...... 600/310; 600/317; 600/342; 422/82.11
(58) Field of Classification Search .................. 600/310, 600/314, 317, 322, 342; 385/12; 356/317, 356/318; 422/82.05, 82.11
See application file for complete search history.

(56) References Cited

U.S. PATENT DOCUMENTS

| 4,657,855 A | 4/1987 | Corey et al. |
| 4,748,116 A | 5/1988 | Simonsson |
| 4,777,019 A | 10/1988 | Dandekar |
| 4,841,198 A | 6/1989 | Wilhelm |
| 4,846,548 A | 7/1989 | Klainer |
| 5,108,899 A | 4/1992 | Allen |
| 5,111,079 A | 5/1992 | Steele |
| 5,354,825 A | 10/1994 | Klainer et al. |
| 5,464,739 A | 11/1995 | Johnson et al. |
| 5,663,044 A | 9/1997 | Noffsinger et al. |
| 5,750,359 A | 5/1998 | Huh et al. |

(Continued)

FOREIGN PATENT DOCUMENTS

EP 0482960 A1 1/1992

(Continued)

OTHER PUBLICATIONS

Fleminger, G. et al., "Fluorogenic Substrates for Bacterial Aminopeptidase P and Its Analogs Detected in Human Serum and Calf Lung," European Journal of Biochemistry, v. 125, pp. 609-615, 1982.*

(Continued)

*Primary Examiner* — Eric Winakur
(74) *Attorney, Agent, or Firm* — Dority & Manning, P.A.

(57) ABSTRACT

Disclosed herein are methods and devices for detection of hospital acquired infections. Disclosed methods may be utilized for continuous in vivo monitoring of a potential infection site or for periodic in vitro monitoring of tissue or fluid from a patient and may be utilized to alert patients and/or health care providers to the presence of a pathogen at an early stage of infection. Disclosed methods utilize fluorophore pairs that optically interact with one another according to Forster resonance energy transfer (FRET) or bioluminescence resonance energy transfer (BRET) mechanism. One member of the pair or a cofactor that interacts with an enzyme to form a member of the pair may be tethered to a device by a substrate that is specific for an enzyme expressed by a targeted pathogen. Upon interaction of the enzyme with the substrate, an optically detectable signal may be altered or initiated, detection of which may then provide information as to the existence of the pathogen at the site.

26 Claims, 7 Drawing Sheets

U.S. PATENT DOCUMENTS

| | | | |
|---|---|---|---|
| 5,786,137 | A | 7/1998 | Diamond et al. |
| 5,812,723 | A | 9/1998 | Ohtsu et al. |
| 5,862,803 | A | 1/1999 | Besson et al. |
| 5,935,799 | A * | 8/1999 | Isbister ............... 422/82.05 |
| 5,985,166 | A | 11/1999 | Unger |
| 6,040,194 | A | 3/2000 | Chick et al. |
| 6,117,090 | A | 9/2000 | Caillouette |
| 6,289,238 | B1 | 9/2001 | Besson et al. |
| 6,441,747 | B1 | 8/2002 | Khair et al. |
| 6,485,926 | B2 | 11/2002 | Nemori |
| 6,521,109 | B1 | 2/2003 | Bartic et al. |
| 6,602,702 | B1 | 8/2003 | McDevitt et al. |
| 6,659,947 | B1 | 12/2003 | Carter et al. |
| 6,802,811 | B1 | 10/2004 | Slepian |
| 6,870,235 | B2 | 3/2005 | Abstreiter et al. |
| 7,096,053 | B2 | 8/2006 | Loeb et al. |
| 7,235,389 | B2 | 6/2007 | Lim et al. |
| 7,294,105 | B1 | 11/2007 | Islam |
| 7,473,548 | B2 | 1/2009 | Soykan et al. |
| 7,846,722 | B2 * | 12/2010 | Williams et al. ............... 435/325 |
| 2002/0182627 | A1 | 12/2002 | Wang et al. |
| 2003/0139667 | A1 | 7/2003 | Hewko et al. |
| 2004/0078219 | A1 | 4/2004 | Kaylor et al. |
| 2005/0096516 | A1 | 5/2005 | Soykan et al. |
| 2005/0101841 | A9 | 5/2005 | Kaylor et al. |
| 2005/0118603 | A1 * | 6/2005 | Chun et al. ............... 435/6 |
| 2005/0260660 | A1 | 11/2005 | Van Dongen et al. |
| 2005/0267326 | A1 | 12/2005 | Loeb et al. |
| 2006/0177891 | A1 | 8/2006 | Kishen et al. |
| 2006/0275822 | A1 | 12/2006 | Miyawaki et al. |

FOREIGN PATENT DOCUMENTS

| | | |
|---|---|---|
| WO | WO 9109312 A1 | 6/1991 |
| WO | WO 9400602 A1 | 1/1994 |
| WO | WO 0185637 A2 | 11/2001 |
| WO | WO 03083454 A1 | 10/2003 |
| WO | WO 2005094285 A2 | 10/2005 |
| WO | WO 2006086878 A1 | 8/2006 |

OTHER PUBLICATIONS

Lakowicz, et al., "Emerging Biomedical and Advanced Applications of Time-Resolved Fluorescence Spectroscopy" *Journal of Fluorescence*, vol. 4, No. 1, 1994.

Rainone et al., U.S. Appl. No. 11/954,881, filed Dec. 12, 2007, Implantable Devices for Fiber Optic Based Detection of Nosocomial Infection.

Rainone et al., U.S. Appl. No. 11/959,823, filed Dec. 19, 2007, Field Effect Transistors for Detection of Nosocomial Infection.

Rainone et al., U.S. Appl. No. 11/954,867, filed Dec. 12, 2007, Fiber Optic Based Detection of Autofluorescent Bacterial Pathogens.

Plowman et al., U.S. Appl. No. 11/955,779, filed Dec. 13, 2007, Recombinant Bacteriophage for Detection of Nosocomial Infection.

Abstract of Japanese Patent No. JP11056398, Mar. 2, 1999.

Ko et al., *A novel FRET-based optical fiber biosensor for rapid detection of Salmonella typhimurium*, Biosensors and Bioelectronics, vol. 21, Issue 7, Jan. 15, 2006, pp. 1283-1290.

Search Report and Written Opinion for PCT/IB2008/053652 dated Aug. 26, 2009, 12 pages.

Chen, et al., "Mechanism of Fluorescence Concentration Quenching of Carboxyfluorescein in Liposomes: Energy Transfer to Nonfluorescent Dimers", Analytical Biochemistry, 172, 61-77 (1988).

Dubin, Greggorz, Extracellular Proteases of *Staphylococcus* spp., Biological Chemistry, vol. 383, pp. 1075-1086, Jul./Aug. (2002).

Giana, et al., Rapid Identification of Bacterial Species by Fluorescence Spectroscopy and Classification Through Principal Components Analysis, Journal of Fluorescence, vol. 13, No. 6, pp. 489-493 (Nov. 2003).

Abstract—Goguen, et al., "Proteases and bacterial virulence: a view from the trenches.", Infect Agents Dis. March; vol. 4(1), pp. 47-54, (1995).

Abstract—JP03210193 A, "Measuring Instrument for Hydrolase", Published Sep. 13, 1991.

Lu, et al. "Shaping biodegradable polymers as nanostructures: Fabrication and applications", Drug Discovery Today: Technologies, vol. 2, No. 1, 2005 pp. 97-102.

Abstract—Lyczak, et al., "Establishment of *Pseudomonas aeruginosa* infection: lessons from a versatile opportunist", Microbes and Infection, vol. 2, Issue 9, Jul. 2000, pp. 1051-1060.

Marquart, et al., "Identification of a Novel Secreted Protease from *Pseudomonas aeruginosa* that Causes Corneal Erosions", Investigative Ophthalmology & Visual Science, vol. 46, No. 10, pp. 3761-3768 (2005).

Plowman et al., "Femtomolar sensitivity using a channel-etched thin film waveguide fluoroimmunosensor," Biosensors & Bioelectronics, vol. 11, No. 1/2, pp. 149-160 (1996).

Abstract—Plowman et al., "Multiple-Analyte Fluoroimmunoassay Using an Integrated Optical Waveguide Sensor (Abstract)," Anal. Chem. vol. 71, No. 19, pp. 4344-4352 (1999).

Plowman, "Silicon oxynitride integrated optical waveguide fluoroimmunosensor: multiple analyte sensing," Doctoral Dissertation, Duke University, 1999.

Plowman et al., "Surface sensitivity of SiON integrated optical waveguides (IOWs) examined by IOW-attenuated total reflection spectrometry and IOW-Raman spectroscopy," Thin Solid Films, vol. 243, pp. 610-615 (1994).

Plowman et al., "Waveguide Multi-Channel Immunoassay using Photo-deprotection Immobilization," SPIE vol. 3603, pp. 163-169 (Jan. 1999).

Utzinger et al., "Fibre Optic Probes in Optical Spectroscopy, Clinical Applications," Encyclopedia of Spectroscopy and Spectrometry, Academic Press, pp. 512-528 (1999).

Utzinger et al., "Fibre Optic Probes in Optical Spectroscopy", Journal of Biomedical Optics vol. 8(1), pp. 121-147 Jan. 2003.

Xu, et al., A bioluminescence resonance energy transfer (BRET) system: Application to interacting circadian clock proteins Proc. Natl. Acad. Sci. USA, vol. 96, pp. 151-156, (Jan. 1999).

* cited by examiner

RESONANCE ENERGY TRANSFER BASED DETECTION OF NOSOCOMIAL INFECTION

BACKGROUND

Nosocomial or hospital acquired infections (HAI) have been estimated by the World Health Organization (WHO) to kill between 1.5 and 3 million people every year worldwide. Though commonly referred to as hospital acquired infections, nosocomial infections result from treatment in any healthcare service unit, and are generally defined as infections that are secondary to the patient's original condition. In the United States, HAIs are estimated to occur in 5 percent of all acute care hospitalizations, resulting in more than $4.5 billion in excess health care costs. According to a survey of U.S. hospitals by the Centers for Disease Control and Prevention (CDC), HAIs accounted for about 1.7 million infections and about 99,000 associated deaths in 2002. The CDC reported that "[t]he number of HAIs exceeded the number of cases of any currently notifiable disease, and deaths associated with HAIs in hospitals exceeded the number attributable to several of the top ten leading causes of death in U.S. vital statistics" (Centers for Disease Control and Prevention, "Estimates of Healthcare Associated Diseases," May 30, 2007).

HAIs, including surgical site infections (SSIs), catheter related blood stream infections (CRBSIs), urinary tract infections (UTIs), ventilator associated pneumonia (VAP), and others, may be caused by bacteria, viruses, fungi, or parasites. For instance, bacterial organisms, such as *Escherichia coli*, *Staphylococcus aureus*, and *Pseudomonas aeruginosa* are common causes as are yeasts such as *Candida albicans* and *Candida glabrata*, fungi such as those of the genus *Aspergillus* and those of the genus *Saccharomyces*, and viruses such as parainfluenza and norovirus.

Ongoing efforts are being made to prevent HAI through, for instance, improved hand washing and gloving materials and techniques, but such efforts have met with limited success. In an effort to better understand and curb HAIs, government regulations have increased pressure on hospitals and care-givers to monitor and report these types of infections. However, these measures are further complicated due to the prevalence of outpatient services, a result of which being that many HAIs do not become evident until after the patient has returned home. As such, infection may proceed undiagnosed for some time, complicating treatment and recovery.

A need currently exists for improved methods for diagnosing HAI. Moreover, methods that could monitor a patient, for early signs of HAI in an outpatient setting, would be of great benefit.

SUMMARY

In accordance with one embodiment, a method for detecting the presence or amount of a pathogen that is a source of a hospital acquired infection comprising is disclosed. In one embodiment may include locating an optical fiber in an environment, the optical fiber having directly or indirectly attached thereto a first group of molecules. The group of molecules includes an acceptor molecule. In addition, one of the molecules of the group may be attached to the optical fiber with a tether that includes a substrate, and the substrate is the target of an enzyme that is expressed by the pathogen. The method may also include transmitting an excitation signal specific for a donor molecule via the optical fiber.

In the presence of the enzyme that is expressed by the targeted pathogen, the substrate of the tether may be cleaved. The method may also include transmitting an optically detectable emission signal from the site following the cleavage of the tether and determining the presence or amount of the pathogen in the environment.

Also disclosed herein are portable devices for detecting the presence or amount of a pathogen. A device may include, for example, a portable enclosure containing a power source, an optical detector, a signal processor, and a signaling device for emitting a signal upon detection of an enzyme that is expressed by the pathogen. A device may also include a connecting device for attaching the enclosure to the clothing or body of a wearer and a fiber optic cable for inserting into the environment of inquiry, the fiber optic cable being in optical communication with the optical detector and extending for a length exterior to the enclosure. In addition, the fiber optic cable may include an optical fiber that directly or indirectly carries a group of molecules, e.g., a FRET pair or a BRET group.

Other features and aspects of the present disclosure are discussed in greater detail below.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which.

Figure 1:
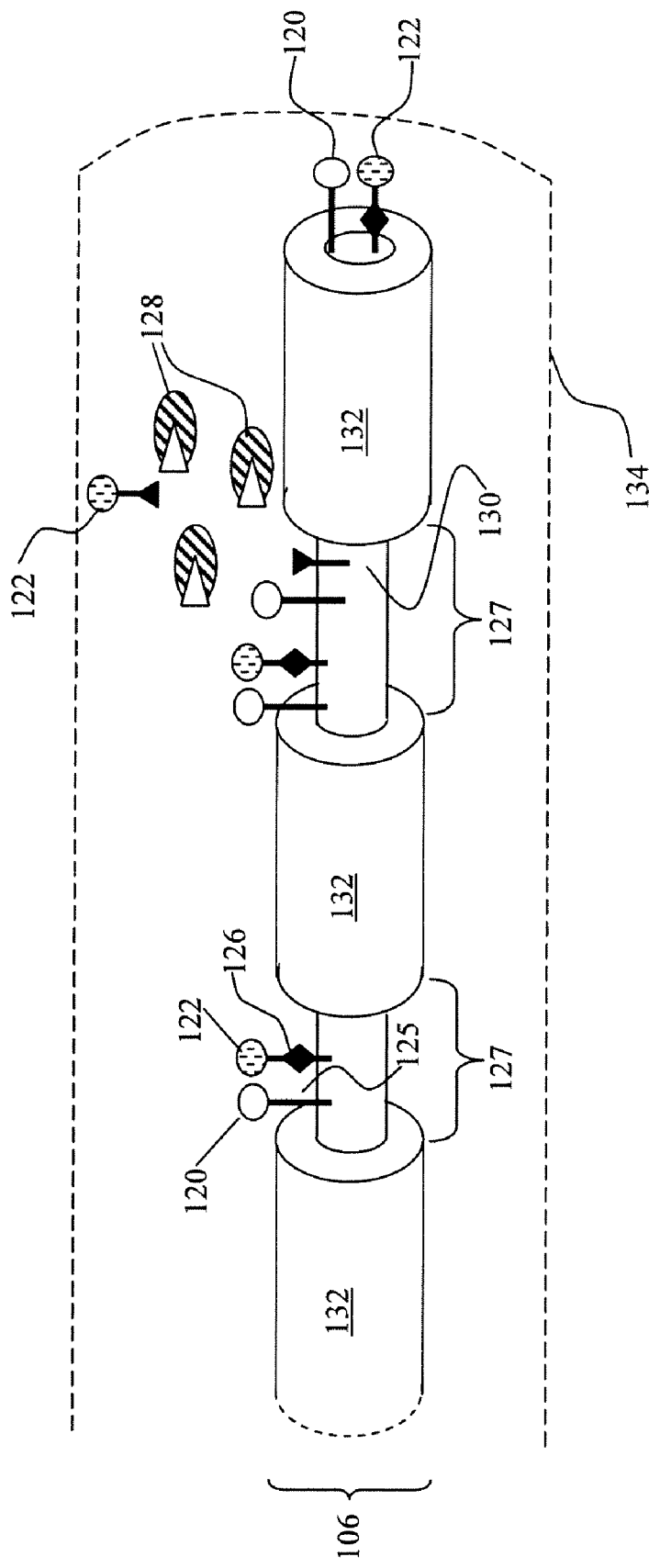
FIG. 1 is a schematic representation of one embodiment of a pathogen detection process as described herein.

Repeat use of reference characters in the present specification and drawings is intended to represent same or analogous features or elements.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

The present disclosure is generally directed to methods for detection of HAI, i.e., nosocomial infection. In one embodiment, disclosed methods may be utilized for continuous in vivo monitoring of a potential infection site and may be utilized to alert patients and/or health care providers to the presence of pathogens at an early stage of infection, thereby providing for earlier intervention and improved recovery rates from infection. In another embodiment, disclosed methods may be utilized for in vitro testing protocols to determine the presence of pathogens in a fluid or tissue sample obtained from a patient.

Any source of HAI may be detected according to disclosed methods. For instance, while common bacterial sources such as *Escherichia coli, Staphylococcus aureus*, and *Pseudomonas aeruginosa* may be of particular interest in certain embodiments, disclosed methods are not limited to these bacteria. Other common sources of HAI that may be detected according to disclosed methods include, without limitation, other bacterial sources such as coagulase-negative *staphylococci, Enterococcus* spp., *Enterobacter* spp., *Klebsiella pneumoniae, Proteus mirabilis, Streptococcus* spp., and so forth, as well as yeast, fungal, viral, and parasitic sources, as previously mentioned.

Detection regimes as disclosed herein utilize fiber optics-based detection of optical signals from a molecular pair, the members of which interact with one another according to a resonance energy transfer (RET) mechanism. Specifically, molecular pairs may interact with one another according to a Förster resonance energy transfer (FRET) mechanism, and in one embodiment, according to a bioluminescence resonance energy transfer (BRET) mechanism. According to disclosed methods, an optically detectable signal emitted from a pair of molecules that may couple to one another according to a RET mechanism may be initiated, terminated, or altered due to the presence of a targeted pathogen. Thus, detection of a characteristic change in optical signal from the pair may signify the presence of a pathogen and the possibility of an HAI.

FRET and BRET are known mechanisms in which a non-radiative, long-range, dipole-dipole coupling between a donor molecule and an acceptor molecule may transfer energy from the donor to the acceptor. According to both the FRET and BRET mechanisms, a donor molecule in its excited state describes an emission peak that overlaps the excitation peak of an acceptor molecule. As such, when the two are in close enough proximity (generally between about 1 nm and about 10 nm) and the donor is in its excited state, energy may be transferred from the donor to the acceptor and emission from the system will be predominantly defined according to the optical characteristics of the acceptor. In contrast, when the distance between the two is large, such that resonant energy coupling between the two does not take place, and the donor is in its excited state, the donor emission characteristics will dominate. The magnitude of an acceptable distance between the two materials that may ensure energy transfer from the donor to the acceptor according to the RET mechanism is dependent on the spectral properties of the donor and acceptor, as is known in the art.

BRET is a form of FRET. According to a BRET mechanism, a donor and acceptor may be coupled to one another as described above. However, in the case of BRET, the donor molecule may be a bioluminescent molecule that may emit a signal upon interaction with a chemical cofactor. For example, the donor molecule of a BRET pair may be the product of a bacterial luciferase enzymatic reaction. Bacterial luciferase is a mixed function oxidase formed by the association of two protein subunits, α and β. The subunits associate to form a 2-chain complex that catalyzes the flavin-mediated hydroxylation of a long-chain aldehyde (e.g., luciferin) to yield carboxylic acid and an excited flavin. Upon the decay of the flavin to ground state, an optically detectable signal is emitted. Accordingly, a BRET system may utilize a luciferin/luciferase interaction to form the donor molecule of the donor/acceptor pair and need not require an external excitation energy source to initiate energy transfer between the pair members.

A large number of donor and acceptor FRET and BRET pairs are known in the art, including many fluorophores such as green fluorescent protein and color variants thereof. The natural green fluorescent protein is a protein comprised of 238 amino acids (26.9 kDa), originally isolated from the jellyfish *Aequorea victoria/Aequorea aequorea/Aequorea forskalea*, which fluoresces green when exposed to blue light. Multiple variants of green fluorescent proteins are known in the art including, e.g., cyan fluorescent protein (CFP), yellow fluorescent protein (YFP), blue fluorescent protein (BFP), and so forth. Others are described in U.S. Pat. Nos. 5,625,048 and 5,777,079 both to Tsien, et al. (both incorporated herein by reference), which disclose modified GFPs having emission and excitation spectra different to those of wild-type GFPs. U.S. Pat. No. 5,804,387 to Cormack, et al. (incorporated herein by reference) discloses GFP mutants having modified excitation and emission spectra.

Table 1, below, presents a non-limiting listing of donor and acceptor pairs that may be utilized as disclosed herein.

TABLE 1

| Donor | Acceptor |
|---|---|
| Fluorescein | Tetmethylrhodamine (TMR) |
| 5-({[(2-iodoacetyl)amino]ethyl}amino)-naphthalene-1-sulphonic acid (IAEDANS) | Fluorescein |
| IAEDANS | Tryptophan |
| IAEDANS | Alexa Fluor ® 488 |
| IAEDANS | Oregon Green |
| IAEDANS | BODIPY ® FL |
| 5-(2-Aminoethylamino)-1-naphtalene sulfonic acid (EDANS) | 4-(dimethylaminoazo)benzene-4-carboxylic acid (DABCYL) |
| EDANS | [4-dimethylaminoazobenzene-4''-sulfonyl chloride] (DABSYL chloride) |
| Terbium | Alexa Fluor ® 546 |
| Terbium | fluorescein |
| Terbium | GFP |
| Terbium | TMR |
| Terbium | Cyanine 3 (Cy3) |
| Terbium | QSY ® 7 |
| Terbium | R phycoerythrin (R PE) |
| Europium | Cyanine 5 (Cy5) |
| Europium | Allophycocyanin (APC) |
| Europium | Alexa Fluor ® 633 |
| Alexa Fluor ® 488 | Alexa Fluor ® 555 |
| Alexa Fluor ® 488 | Cy3 |
| Alexa Fluor ® 568 | Alexa Fluor ® 647 |
| Alexa Fluor ® 594 | Alexa Fluor ® 647 |
| Alexa Fluor ® 647 | Alexa Fluor ® 594 |
| Cy3 | Cy5 |
| CFP | YFP |
| CFP | dsRED |
| CFP | YFP |
| BFP | GFP |
| GFP | Rhodamine |
| fluorescein isothiocyanate (FITC) | Cy3 |
| FITC | tetramethylrhodamine isothiocyanate (TRITC) |
| aminobenzoic acid (ABZ) | 2,4-dinitrophenol (DNP) |
| DANYSO | Tyr($NO_2$) |
| DANYSL | FAM |
| FAM | TMR |
| Luciferase/luciferin | GFP |
| Luciferase/luciferin | YFP |

In various embodiments, the acceptor may not be fluorescent (see, e.g., Chen, et al. Analytical Biochemistry, 1988, 172:61-77). As the acceptor has a quenching effect on the donor, when the acceptor is not fluorescent, transferred energy may be dissipated through surrounding medium. Thus, in this case, when the donor and acceptor are suitably proximal to one another and the donor is at the excited state, little or no emission will be detected from the pair. Upon separation of the two materials, however, the donor may emit upon excitation at its characteristic emission peak.

FIG. 1 illustrates one representative embodiment of a pathogen detection method as disclosed herein. According to this embodiment, a pair of molecules including a donor 120 and an acceptor 122 may be tethered proximal to one another on an optical fiber 106.

An optical fiber 106 may include a core 130, through which light may travel, and an external cladding layer 132. The difference in the index of refraction between the core material and the clad material defines the critical angle □ at which total internal reflection takes place at the core/clad interface. Thus, light that impinges upon the interface at angle greater than the critical angle is completely reflected, allowing the light to propagate down the fiber.

Optical fiber 106 may generally be a multi-mode fiber having a core diameter greater than about 10 micrometers (μm). The preferred core diameter in any particular embodiment may depend upon the characteristics of excitation light (when required) and/or emission light, among other system parameters. For instance, in those embodiments in which a laser is an excitation source, a core diameter may be between about 50 μm and about 100 μm, for example about 80 μm in one embodiment. In other embodiments, for instance, in those embodiments in which an excitation light source produces less coherent radiation, such as a light emitting diode (LED), for example, it may be preferable to utilize an optical fiber 106 having a larger core diameter, for instance between about 90 μm and about 400 μm.

The boundary between core 130 and clad 132 of a fiber 106 may be abrupt, as in a step-index fiber, or may be gradual, as in a graded-index fiber. A graded index fiber may be preferred in some embodiments, as graded index fibers may reduce dispersion of multiple modes that may be traveling through the fiber. This is not a requirement of disclosed methods, however, and a step-index fiber may alternatively be utilized, particularly in those embodiments in which the optical fiber 106 is of a length such that dispersion will not be of great concern.

Beneficially, an optical fiber 106 may be formed of biocompatible materials that may remain at a site of interest for a relatively long period of time, for instance at an in vivo site. Accordingly, in one embodiment disclosed methods may be utilized to monitor a site for infection throughout the healing process and/or until the high potential for HAI has past. In addition, due to the small cross-section of optical fibers, optical fiber 106 may be easily removed from an in vivo site without the necessity of causing excessive tissue damage at the site.

Core 130 and clad 132 of optical fiber 106 may be formed of any suitable materials that exhibit a suitable difference in refractive index. For instance, suitable glasses may include, without limitation, silica glass, fluorozirconate glass, fluoroaluminate glass, any chalcogenide glass, doped glasses, and so forth as are generally known in the art. Polymer optical fibers (POF) are also encompassed by the present disclosure. For instance, optical fibers formed of suitable acrylate core/clad combinations, e.g., polymethyl methacrylates, may be utilized. It may be preferred in some embodiments to utilize a multi-core POF so as to lower losses common to POF due to bending of the fiber. This may be preferred in those embodiments in which optical fiber 106 is in a non-linear conformation during use.

Referring again to FIG. 1, donor molecule 120 and acceptor molecule 122 may be tethered to optical fiber 106 and proximal to one another such that resonant energy transfer between the two may take place, i.e., between about 1 nm and about 10 nm apart from one another. In general, donor 120 and acceptor 122 may be located at a distance from one another that is up to about twice $R_o$, where $R_o$ is the Förster distance, defined as the distance at which energy transfer is 50% efficient. In other words, $R_o$ is the distance where 50% of excited donors are deactivated due to FRET. At $R_o$, there is an equal probability for resonance energy transfer and the radiative emission of a photon. The efficiency of energy transfer measures the degree of overlap between the donor emission spectrum and acceptor absorption spectrum. This allows for determination of proximity and relative orientation of the members of the pair. In addition, donor molecule 120 and acceptor molecule 122 may be tethered to optical fiber 106 such that optical emissions from the pair may enter and be transmitted along the core 130 of the fiber 106.

For instance, donor molecule 120 and acceptor molecule 122 may be tethered to optical fiber 106 at the terminus of fiber 106, as shown. Donor molecule 120 and acceptor molecule 122 pairs may also be tethered at areas 127 along fiber 106 where all or a portion of clad 132 has been removed. In particular, donor molecule 120 and acceptor molecule 122 may be tethered within the evanescent field of core 130. Methods of removing all or a portion of clad 132 are known in the art, any of which may be utilized to form an area 127 within which a donor/acceptor pair may be tethered within the evanescent field of the core 130. For instance, a solution comprising hydrofluoric acid may be applied to a portion of fiber 106 for a period of time so as to dissolve the clad in that portion. In another embodiment, mechanical abrasion may be utilized to remove a portion of the clad 132.

Donor molecule 120 may be tethered to fiber 106 via a tether 125 using any of a variety of well-known techniques. For instance, covalent attachment of the donor molecule 120 to the fiber 106 may be accomplished using carboxylic, amino, aldehyde, bromoacetyl, iodoacetyl, thiol, epoxy and other reactive or linking functional groups. In another embodiment, a surface absorption technique could be utilized, in which the tethers may simply absorb to the fiber upon incubation.

Acceptor molecule 122 may be tethered to fiber 106 via tether 126. In various embodiments, tether 126 includes a substrate. The term "substrate" generally refers to a substance that is chemically acted upon by an enzyme to form a product. According to this particular embodiment, tether 126 includes a substrate that may be cleaved by an enzyme that is expressed by a pathogenic source of HAI.

Substrates as may be included in a tether 126 may be acted on by various types of enzymes as may be expressed by HAI pathogens. For instance, a substrate tether 126 may be acted on by hydrolases, lyases, and so forth. In some embodiments, the enzyme is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may cleave a tether 126. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may cleave tether 126. "Proteases" are hydrolytic enzymes that cleave peptide bonds found in longer peptides and proteins. Examples of proteases that may cleave tether 126 according to the present disclosure include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases.

The substrate may occur naturally or be synthetic. Some suitable substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Specific types of substrates may include, for instance, proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; U.S. Pat. No. 6,485,926 to Nemori, et al., which are incorporated herein in their entirety by reference thereto for all purposes.

In one particular embodiment, leukocyte esterase may cleave tether 126. Determination of the presence of leukocyte esterase in a sample or in an in vivo location may assist in the diagnosis of hospital acquired urinary tract infection. When detecting leukocyte esterase, for example, the substrate of tether 126 may be an ester that is catalytically hydrolyzed in the presence of leukocyte esterase.

Lactate esters may be included in tether 126, such as described in U.S. Pat. No. 5,464,739 to Johnson, et al. and U.S. Pat. No. 5,663,044 to Noffsinger, et al., which are incorporated herein in their entirety by reference thereto. Lactate esters are generally hydrolyzed by leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750,359 to Huh, et al.; U.S. Pat. No. 4,657,855 to Corey, et al.; and Japanese Publication No. 03210193 to Kawanishi, et al., which are incorporated herein in their entirety by reference thereto.

Bacteria of the genus *Staphylococci* are known to produce several extracellular proteases, including serine, cysteine, and metallo-enzymes (see, e.g., Dubin, Biol. Chem., 383:7-8, 2002, 1075). Accordingly, when detecting HAI due to any of a variety of *Staphylococci* pathogens, the substrate of tether 126 may include a serine residue that may be preferentially cleaved by a serine protease produced by a targeted *Staphylococci* bacterium.

*Pseudomonas aeruginosa*, a relatively common bacterial source of HAI, has been found to express several well characterized enzymes. For instance, *P. aeruginosa* is known to produce elastase B, a metalloprotease that degrades elastin. *P. aeruginosa* also express protease IV, protein targets for which include fibrinogen, plasminogen, IgG, and so forth, and alkaline protease, a metalloprotease that cleaves polylysine.

In yet another embodiment, an aspartyl protease may cleave the substrate of tether 126, for instance in detection of infection due to *Candida albicans*, which is known to express a variety of specific aspartyl proteases. When targeting an aspartyl protease, a tether 126 may include an aspartic acid residue-containing substrate. For instance, a substrate for detection of an aspartyl protease may include two highly-conserved aspartates in the active site.

Acceptor molecule 122 may be tethered to fiber 106 via a tether 126 using any of a variety of well-known techniques. For instance, covalent attachment of the acceptor molecule 122 to the fiber 106 may be accomplished using chemistry similar to that as is used to attach donor molecule 120 to the fiber 106, or a different chemistry, as desired. For instance, acceptor molecule 122 may be covalently attached to fiber 106 via tether 126 using carboxylic, amino, aldehyde, bromoacetyl, iodoacetyl, thiol, epoxy and other reactive or linking functional groups, as well as residual free radicals and radical cations, through which a protein coupling reaction may be accomplished, for instance in those embodiments in which tether 126 includes a proteinaceous substrate. Preferred attachment methods may generally depend upon the nature of the acceptor molecule 122 and the substrate of tether 126, as is known in the art.

With reference to FIG. 1, donor molecule 120 and acceptor molecule 122 may be tethered within the evanescent field of core 130, as shown. However, it should be understood that in general, donor molecules and acceptor molecules need not be provided in a 1:1 ratio to one another. For instance, in other embodiments, it may be preferred to provide a large number of acceptor molecules for each donor molecule, to increase the acceptor emission signal due to RET.

Upon excitation of donor molecule 120, for instance upon transmission of an appropriate excitation signal through fiber 106 to donor molecule 120, resonant energy transfer may occur between the members of the pair and emission from the pair may be dominated by the optical characteristics of acceptor molecule 122. In the presence of enzyme 128, however, the substrate of tether 126 may be cleaved by the action of enzyme 128. Thus, when enzyme 128 is present, acceptor molecule 122 may diffuse away from fiber 106 and emission from the pair may alter and come to be dominated by the optical characteristics of donor molecule 120. Detection of the change in emission from the pair upon loss of the acceptor molecule 122 may signify the presence of enzyme 128. Moreover, as enzyme 128 is an expression product of a pathogenic source of HAI, determination of the presence of enzyme 128 at the site of enquiry may likewise signify the presence of the pathogenic source of enzyme 128 and as such provide a route for early diagnosis and treatment of HAI.

In various embodiments, a barrier 134 may be included in a system to protect fiber 106 from an external environment. For instance, Barrier 134 may be a semi-permeable barrier defining a porosity that may allow enzyme 128 to pass through barrier 134 and interact with tether 126, while preventing passage of other materials. For instance, barrier 134 may prevent a pathogen from contacting fiber 106. Barrier 134 may keep other potential contaminants away from fiber 106 as well. For instance, when considering a system for us in vivo, barrier 134 may prevent materials that may be common at the detection site, e.g., toxins, ECM components, leukocytes, red blood cells, and so forth, from contacting and/or blocking communication between the core of fiber 106 and the donor/acceptor pairs (120, 122) attached thereto.

Barrier 134 may be, for instance, a semi-permeable porous membrane having a porosity to allow materials less than about 0.2 μm across the membrane, with a preferred pore size generally depending upon the size of enzymes 128 that may pass across barrier 134. Semi-permeable membrane 134 may be, for example, derived from a water insoluble, water wettable cellulose derivative, such as cellophane, cellulose acetate, cellulose propionate, carboxyethyl cellulose, and so forth; insolubilized gelatin; partially hydrolyzed polyvinyl acetate; or polyionic film forming compositions such as polysulfonated anionic polymers or ionically linked polycationic polymers, such as marketed by Amicon Company. Barrier 134 may surround fiber 106, as shown, and may be attached to fiber at a distance from the terminus of fiber 106 (not shown) or optionally may be attached to another component of a sensing system, aspects of which are discussed herein.

Figure 2:
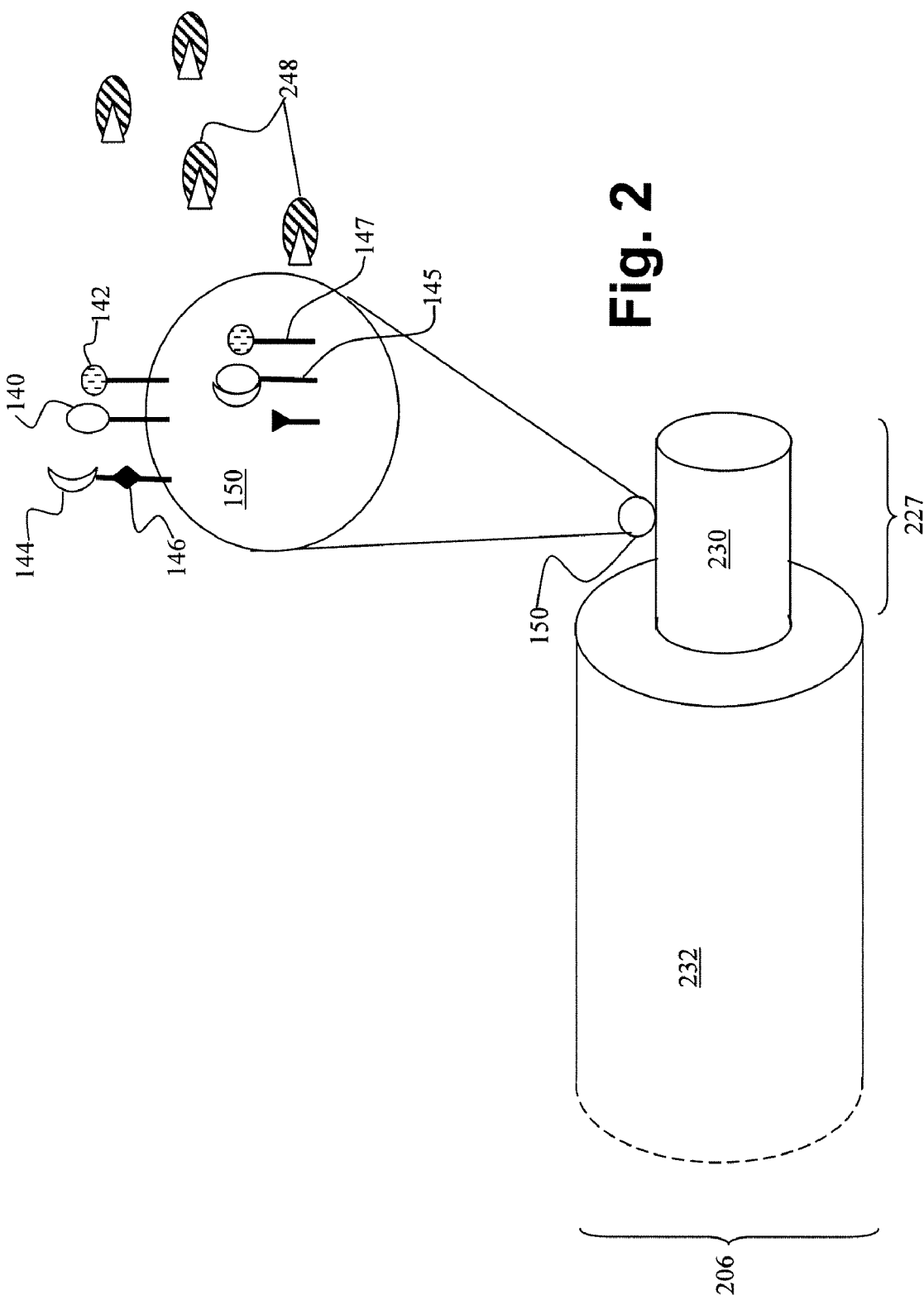
FIG. 2 is a schematic representation of another embodiment of a pathogen detection process as described herein.

FIG. 2 schematically illustrates one method of detection according to a BRET mechanism. As may be seen, in addition to an acceptor molecule 142, a system may include a chemical cofactor 144 and an enzyme 140 that may interact with one another to form a donor molecule in its excited state. For instance, enzyme 140 may be luciferase and cofactor 144 may be luciferin.

Enzyme 140, acceptor molecule 142, and cofactor 144 may be tethered to particle 150 (sometimes referred to as a "bead" or "microbead"). For instance, naturally occurring particles, such as plasmids, plastids, polysaccharides (e.g., agarose), etc., may be used. Further, synthetic particles may also be utilized. For example, in one embodiment, latex particles may be used. While any latex particles may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof.

When utilized, the shape of the particles may generally vary. In the embodiment illustrated in FIG. 2, for instance, particle 150 is spherical in shape. However, it should be understood that other shapes are also contemplated by the present disclosure, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

According to a BRET mechanism, acceptor molecule 142 may be tethered to particle 150 via covalent attachment of the acceptor molecule 142 to the particle 150 via tether 147, as shown. In addition, one of the cofactor and the enzyme of the donor formation pair may be attached to the particle via a tether that includes a substrate for an enzyme expressed by a pathogen. For instance, according to the embodiment illustrated in FIG. 2, chemical cofactor 144 is tethered to particle 150 via tether 146 that includes a substrate for an enzyme expressed by a pathogen and enzyme 140 is tethered to particle 150 via tether 147. In other embodiments, however, the enzyme of the pair that interacts to form the donor molecule may be attached via a tether that includes a substrate specific for a pathogen-expressed enzyme.

The enzyme 140, acceptor molecule 142, and cofactor 144, may generally be attached to particle 150 using any of a variety of well-known techniques, as discussed above, e.g., carboxylic, amino, aldehyde, bromoacetyl, iodoacetyl, thiol, epoxy and other reactive or linking functional groups, and so forth. A surface functional group of particle 150 may also be incorporated in a tether as a functionalized co-monomer because the surface of the particle may contain a relatively high surface concentration of polar groups. In addition, although particles may be functionalized after synthesis, such as with poly(thiophenol), particles may be capable of direct covalent linking with a tether, e.g., a protein, without the need for further modification.

For example, in one embodiment, the first step of conjugation of a substrate tether 146, a tether 145, and a tether 147 with particle 150 is activation of carboxylic groups on the surface of particle 150 using carbodiimide. In the second step, the activated carboxylic acid groups are reacted with an amino group of the substrate of tether 146, tether 145 and tether 147 to form an amide bond. The activation and/or protein coupling may occur in a buffer, such as phosphate-buffered saline (PBS) (e.g., pH of 7.2) or 2-(N-morpholino) ethane sulfonic acid (MES) (e.g., pH of 5.3). Cofactor 144, donor molecule 140 and acceptor molecule 142 may be bound to their respective tethers 146, 145, and 147 prior to attachment of the tethers to the particle, during the attachment process or following, as desired. The resulting particles may then be contacted with ethanolamine, for instance, to block any remaining activated sites. Overall, this process forms a conjugated probe, where the cofactor 144, the enzyme 140 and the acceptor molecule 142 are covalently attached to the particle 150.

Utilization of a particle for attachment of components of a RET method is not a requirement for any particular embodiment of the disclosed subject matter. For instance, a FRET mechanism in which the donor molecule is excited from an exogenous optical source may include particles for tethering and holding components of the system, as described in FIG. 2 for a BRET mechanism. Similarly, the components of a BRET process may be tethered directly to an optical fiber, as discussed above with regard to the FRET mechanism of FIG. 1.

Referring again to FIG. 2, particle 150 may be held near core 230 such that emissions from the donor/acceptor pair may be transmitted through fiber 206. For instance, particle 150 carrying enzyme 140, acceptor molecule 142, and cofactor 144 may be adhered to optical fiber 206 at the terminus of fiber 206 as well as at locations 227 along fiber 206 where all or a portion of clad 232 has been removed. Particle 150 may be covalently bound to core 230, for instance via carbodiimide chemistry, as described above for the formation of the conjugated particle or according to any other suitable chemistry as is known in the art. Alternatively, particle 150 may be coupled to core 230 through non-covalent coupling, for instance through charge coupling. For example, when the particle carries an opposite surface charge as does the core 230 the two may be ionically bound to one another. Any other suitable binding method may alternatively be utilized. In any case, particle 150 may be adhered to fiber 206 such that enzyme 140 and acceptor molecule 142 may be held within the evanescent field of core 230 and such that the tether 146 holding cofactor 144 in place is able to be exposed to the surrounding environment. Upon interaction of an enzyme 248 expressed by a targeted pathogen with tether 146, cofactor 144 may be released. As cofactor 144 is tethered near enzyme 140, generally at a distance of about 10 nm or less, cofactor 144 may interact with enzyme 140, leading to the formation of a donor molecule in its excited state and RET-mediated transfer of energy to acceptor molecule 142. Determination of an emission from the pair that is characteristic of the acceptor molecule 142 may signify the presence of enzyme 148 and thus the pathogenic source of the enzyme 148.

Figure 3:
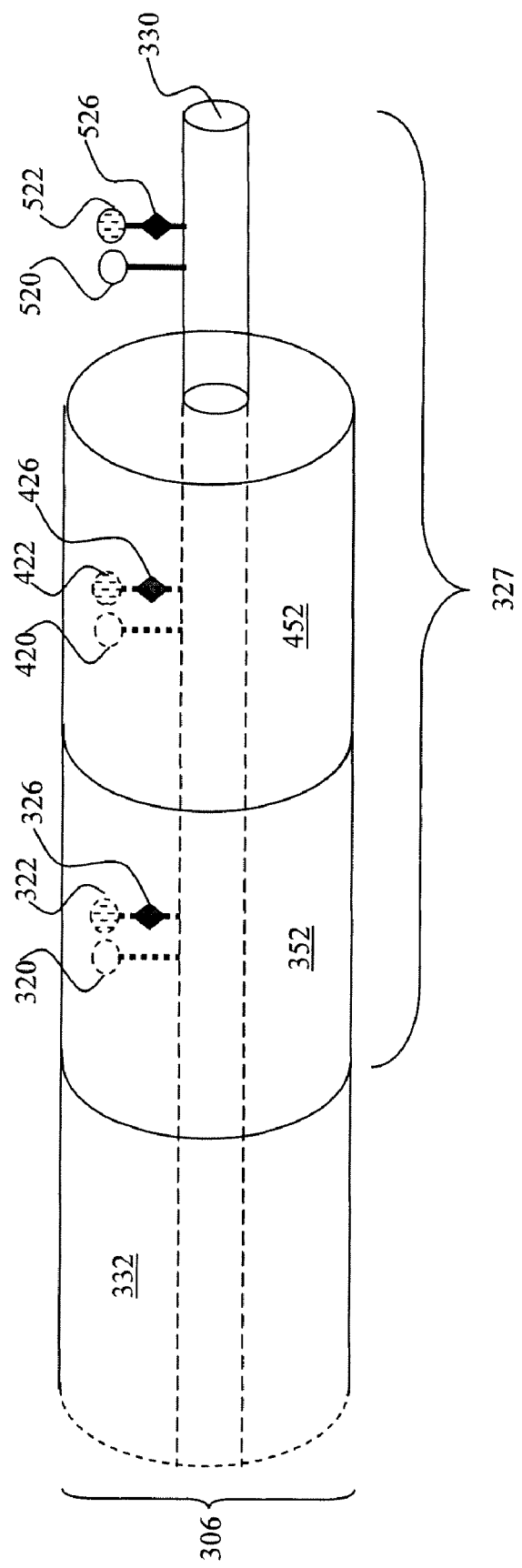
FIG. 3 is a schematic representation of another embodiment of a pathogen detection process as described herein.

FIG. 3 schematically illustrates another embodiment of a method and device as disclosed herein. According to this particular embodiment, the clad 332 of fiber 306 has been removed along a length of the fiber to form area 327 along which the core 330 may extend. In addition, several pairs of molecules (320, 322), (420, 422), (520, 522) have been tethered to core 330, each pair including a donor molecule (320, 420, 520) and an acceptor molecule (322, 422, 522), respectively. The tethers for the acceptor molecules, 326, 426, 526, include a substrate for an enzyme, as discussed above. In addition, a first degradable matrix 352 encapsulates the first donor/acceptor pair (320, 322) and a second degradable matrix 452, encapsulates the second donor/acceptor pair (420, 422). Thus, during use, the outermost pair of molecules, 520, 522 will be immediately exposed to both the surrounding environment and the evanescent field of the core 330 upon location of the fiber 306 in the field of enquiry. After a period of time, matrix 452 may degrade, exposing the next pair of molecules, 420 and 422 to both the surrounding environment and the evanescent field of the fiber. Finally, the innermost matrix 352 may degrade, exposing the next pair of molecules 320 and 322. Thus, over time, additional RET pairs may be exposed. Protecting the members of a pair for a period of time may prevent the pair members from photobleaching and extend the useful life of the device.

Matrices 352, 452 may be hydrophilic in nature. This may be preferred in certain in vivo detection processes and devices, as a hydrophilic matrix may be less likely to provoke an immuno-suppression response. This is not a requirement of the invention, however, and in other embodiments, a matrix may include a hydrophobic material, e.g., a hydrophobic polymeric matrix.

Either or both of matrices 352, 452 may be degradable polymeric matrices and in one embodiment, hydrogels. Hydrogels generally include polymeric matrices that may be highly hydrated, e.g., from about 20% to more than 99% water by weight, while maintaining structural stability. Suitable hydrogel matrices may include un-crosslinked and crosslinked hydrogels. In general, the hydrogels may include hydrolyzable portions, e.g., hydrolyzable crosslinks, such that the matrix may be degradable when utilized in an aqueous environment. For example, a matrix may include a crosslinked hydrogel including a hydrolyzable cross-linking agent, such as polylactic acid, and may be degradable in vivo. The degradable matrices may also be formed so as to have predetermined rates of degradation following location of the device at an in vivo site of interest. For instance, matrix 352 may have a slower rate of degradation than does matrix 452.

A degradable polymeric matrix, including hydrogels, may include natural biopolymers such as glycosaminoglycans, polysaccharides, proteins, and so forth, as well as synthetic polymers, as are generally known in the art. A non-limiting list of polymeric materials that may be utilized in forming a hydrogel may include, without limitation, dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins and peptides, and so forth.

A degradable polymeric matrix may be formed according to any method as is generally known in the art. For instance, a matrix may self-assemble upon mere contact of the various components or upon contact in conjunction with the presence of particular external conditions (such as temperature or pH). Alternatively, assembly may be induced according to any known method following mixing of the components. For example, step-wise or chain polymerization of multifunctional monomers or macromers may be induced via photopolymerization, temperature dependent polymerization, and/or chemically activated polymerization. Optionally, a hydrogel may be polymerized in the presence of an initiator. For example, a hydrogel may be photopolymerized in the presence of a suitable initiator such as Irgacure® or Darocur® photoinitiators available from Ciba Specialty Chemicals. In another embodiment, a cationic initiator may be present. For example, a polyvalent elemental cation such as $Ca^{2+}$, $Mg^{2+}$, $Al^{3+}$, $La^{3+}$, or $Mn^{2+}$ may be used. In yet another embodiment, a polycationic polypeptide such as polylysine or polyarginine may be utilized as an initiator.

A degradable polymeric matrix may be formed on or applied to fiber 306 so as to encapsulate the layer of donor/acceptor pairs, as shown. For instance, in the embodiment illustrated in FIG. 3, a first hydrogel matrix 352 may be applied to core 330 along a length that may encapsulate donor 320 and acceptor 322. A second hydrogel matrix 452 may be applied to an adjacent length of core 330 that may encapsulate of donor 420 and acceptor 422. Any method for shaping and applying a degradable matrix to a surface of a fiber as is generally known in the art may be utilized. For instance, a degradable polymer matrix may be shaped according to processes including, without limitation, replication molding techniques such as microimprinting lithography and soft lithography; laser interference lithography, nanosphere lithography techniques such as laser assisted nanospheres lithography and nanosphere 'shadow mask' lithography; block copolymer lithography; and so forth (see, e.g., Lu, et al., Drug Discovery Today: Technologies, 2005, 2:1).

An HAI detection method and device as described herein may include a fiber optic cable comprised of a single optical fiber or a plurality of optical fibers, depending upon the specific design of the device. For instance, a plurality of optical fibers may be joined to form a single fiber cable of a size to be located at an in vivo site of interest (e.g., less than about 1.5 mm in cross-sectional diameter).

Figure 4A:
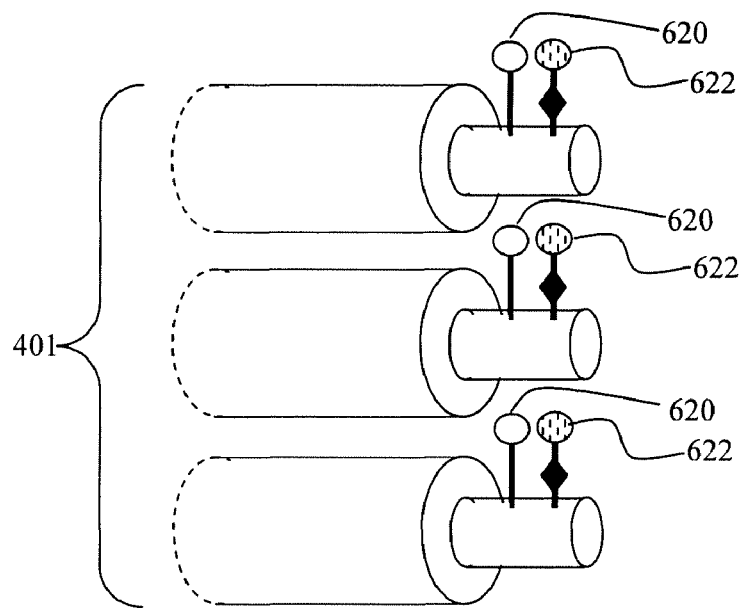
FIGS. 4A-4D are schematic representations of optical fiber cables as may be incorporated in a device as disclosed herein.

When utilizing a plurality of fibers in a fiber bundle or cable, individual fibers may include the same or different donor/acceptor pairs as one another. For instance, FIG. 4A illustrates a fiber cable 401 that includes a plurality of the same donor/acceptor pairs (620, 622) on each fiber. Such an arrangement may be utilized, for instance, to prevent premature destruction of the pair members due to photobleaching. For instance, an excitation signal may be transmitted down only a single or a limited number of fibers at a time and for only a limited amount of time. Following that predetermined period of time, e.g., the period of time at which photobleaching of the donor and/or acceptor is likely to occur, the excitation signal may be transmitted down a second fiber of the cable. Thus, the multi-fiber optical cable may be utilized to detect the presence of enzymes expressed from a pathogen for an extended period of time, without the loss of activity of the device due to photobleaching of members of the RET pairs.

Figure 4B:
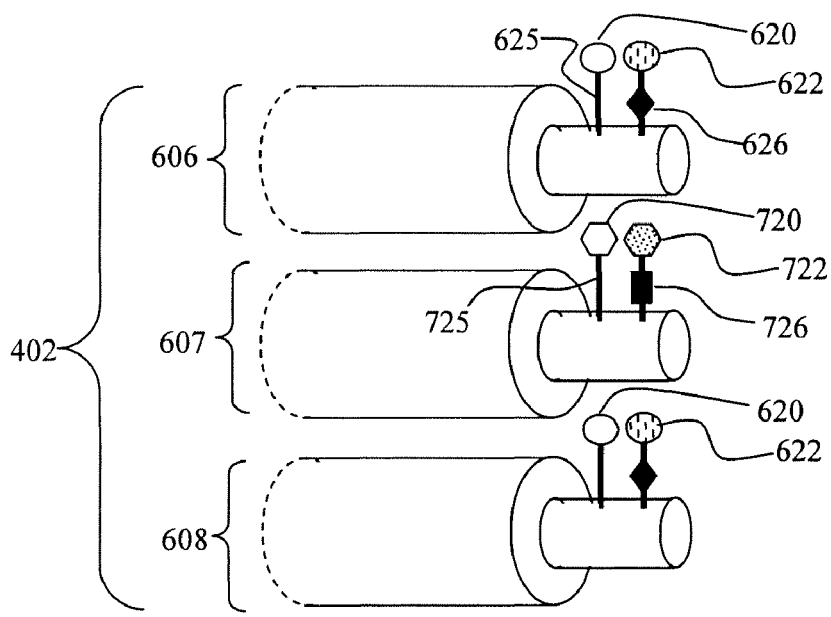

Alternatively, in the embodiment illustrated in FIG. 4B, each fiber of cable 402 may differ from one another in design. For instance, a first fiber of the bundle, 606 may include donor molecule 620 attached to fiber 606 via tether 625 and acceptor molecule 622 attached to fiber 606 via tether 626 that includes a first substrate that may be specific for a first enzyme from a first pathogen. A second fiber of the bundle, 607 may include donor molecule 720 attached to fiber 607 via tether 725 and acceptor molecule 722 attached to fiber 607 via tether 726 that includes a second, different substrate that may be specific for a second enzyme expressed from a second, different pathogen. Donor molecules 620, 720 and acceptor molecules 622, 722, may be the same as one another or different. Thus, an emission signal from the first pair (620, 622) characteristic of the first donor molecule 620 may signify the presence of an enzyme specific for the substrate of tether 626, and hence the pathogen that expresses that enzyme, while an emission signal from the second pair (720, 722) that is characteristic of the second donor molecule 720 may signify the presence of an enzyme specific for the substrate of tether 726, and hence the second pathogen that expresses that second enzyme. In this particular embodiment, a third fiber of the bundle 608 carries the same acceptor donor pair 620, 622, as is carried by fiber 606, though this is not a requirement, and in other embodiments a third fiber may have yet another donor/acceptor pair attached thereto. In yet another embodiment, a third fiber of the bundle may be utilized as an emission transmission fiber. For instance, fiber 606 and fiber 607 may be utilized to transmit excitation signals to the FRET pairs on each fiber, and third fiber 608 may be in optical communication with each fiber 606, 607 and utilized to transmit emissions from the pairs on these fibers back to a sensor.

It may beneficial in this embodiment to avoid spectral overlap between adjacent fibers, particularly if donor molecules 620, 720 and/or acceptor molecules 622, 722 are the same or exhibit overlapping spectral characteristics. For instance, spacers may be placed between the fibers 606, 607, 608, so as to avoid an excitation or emission signal from a first fiber 606 influencing the RET pairs of a second fiber 607.

Figure 4C:
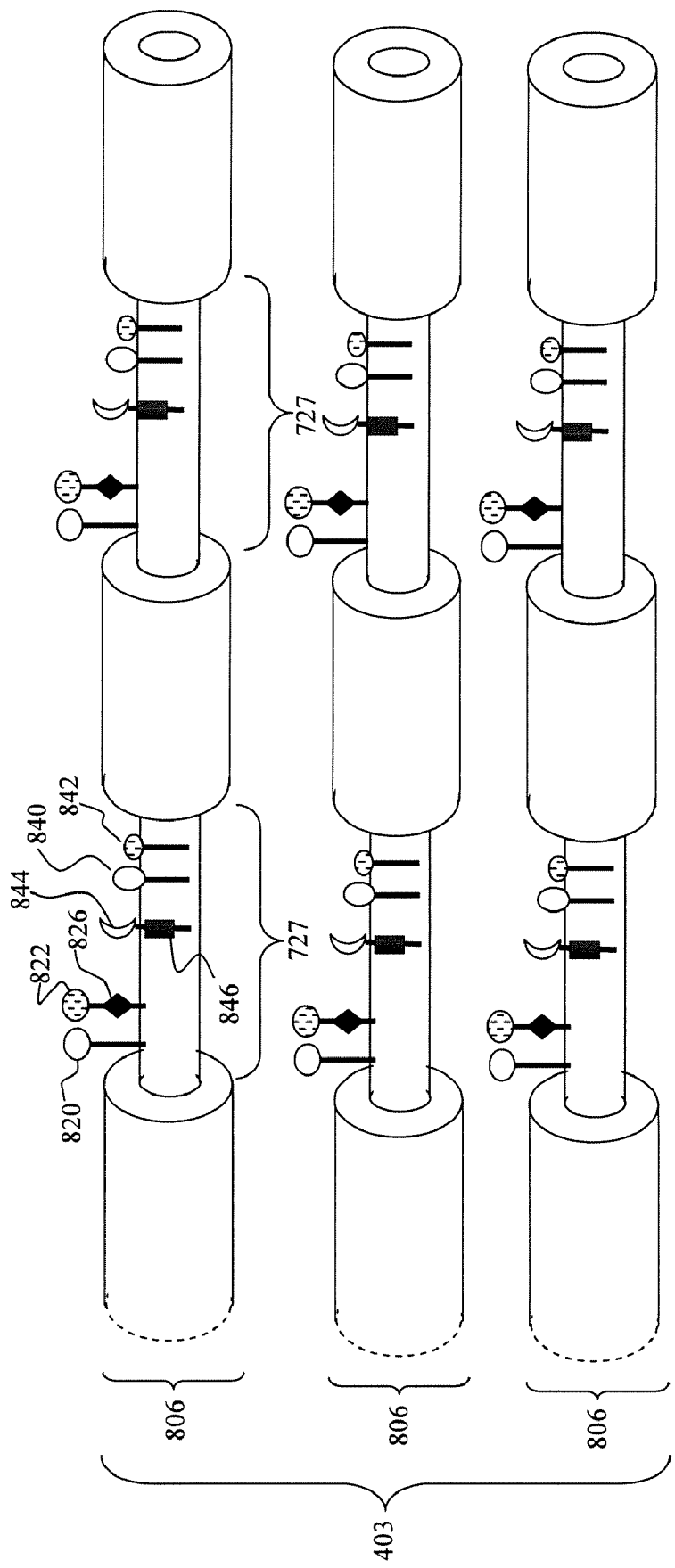

In the embodiment illustrated in FIG. 4C, each fiber 806 of the fiber cable 403 includes a plurality of different RET pairs. For instance, fiber 806 includes areas 727 each of which contain FRET pair 820, 822 with the acceptor molecule 822 tethered to fiber 806 with a tether 826 including a first substrate. Area 727 also includes a second RET pair, in this case a BRET group 840, 842, as well as chemical cofactor 844, that may interact with enzyme 840 to form a donor molecule that may emit a fluorescent signal. The substrate of tether 846, which binds cofactor 844 to fiber 806, may be specific for a different enzyme that that of tether 826. In general, in this embodiment, the various excitation and emission signals of the different RET pairs may be far enough apart from one another in the spectrum so as to be separably detectable by a sensor, as described further herein.

Figure 4D:
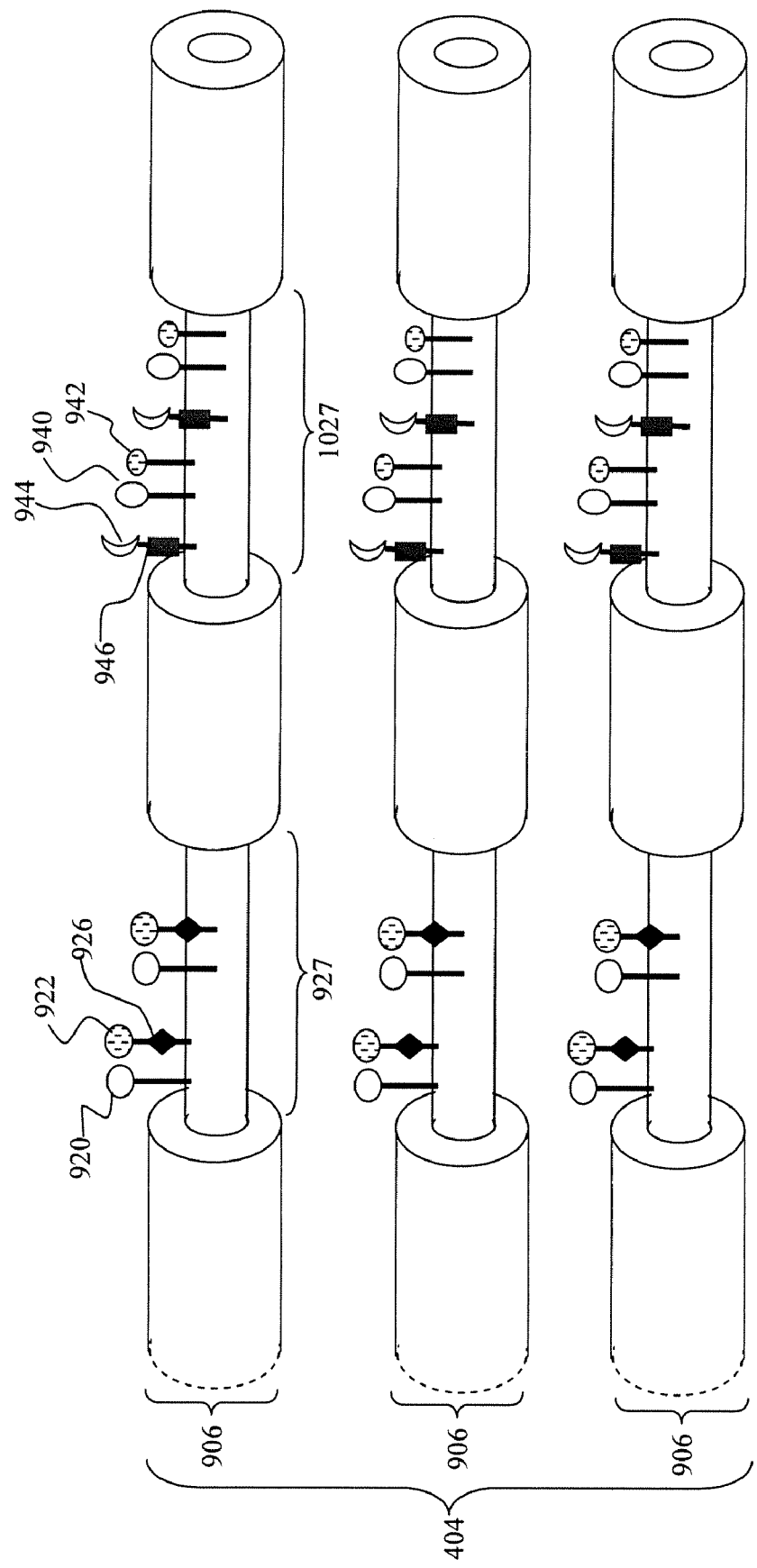

Optionally, different areas of a single fiber may contain different RET pairs. For instance, referring to FIG. 4D, a first area 927 of fiber 906 includes a first type of RET pair bound therein, including donor 920 and acceptor 922, as shown, and a second area of the same fiber may include a different RET pair, in this case a BRET group, including enzyme 940, acceptor 942, and cofactor 944, the cofactor molecule tether 946 being subject to cleavage by a different type of enzyme than the tether 926 of the first pair (920, 922). In this particular embodiment, all of the fibers of the fiber cable 404 have the same design. Of course, combinations of such designs, as well as other variations may be utilized as well.

A plurality of optical fibers may generally be held together as a cohesive unit with any biocompatible glue or adhesive is generally known in the art. For instance, biocompatible adhesives based upon proteins such as gelatins may be utilized, as may those formed from polysaccharides.

An optical fiber including one or more RET pairs as described herein (i.e., a FRET pair or a BRET group) may be placed and held in an environment in which enzymes expressed from pathogens responsible for HAI may exist. For instance, an optical cable including one or more optical fibers may be located at an in vivo site that is a potential site of HAI development. For instance, in one embodiment, an optical cable including one or more RET pairs tethered thereto may be located in vivo at a wound, a catheter site, a surgical site, an endotracheal (ET) tube site, or the like.

An optical cable including one or more RET pairs may be located at a site of inquiry according to any suitable method. For instance, prior to closing a surgical site, an optical cable as described herein may be located within the site. In one embodiment, an optical cable may be located at a site of interest in conjunction with a medical device. For instance an optical cable may be located adjacent to or within a medical device such as a catheter, a surgical drain, an ET tube, or the like, and the medical device may then aid in maintaining the optical cable at the site of interest.

Disclosed methods are not limited to in vivo detection methods. In another embodiment, an optical cable as described herein may be located in an in vitro environment in conjunction with a tissue or fluid sample from a subject. The tissue or fluid sample may contain a pathogenic source of HAI, or alternatively may contain merely protein expression products of a pathogen. In particular, the sample may contain enzymes that may interact with a tether and develop an optically detectable signal in an optical fiber. Detection of the signal may signify the presence of the pathogen in the sample itself or alternatively in the source of the sample.

Figure 5:
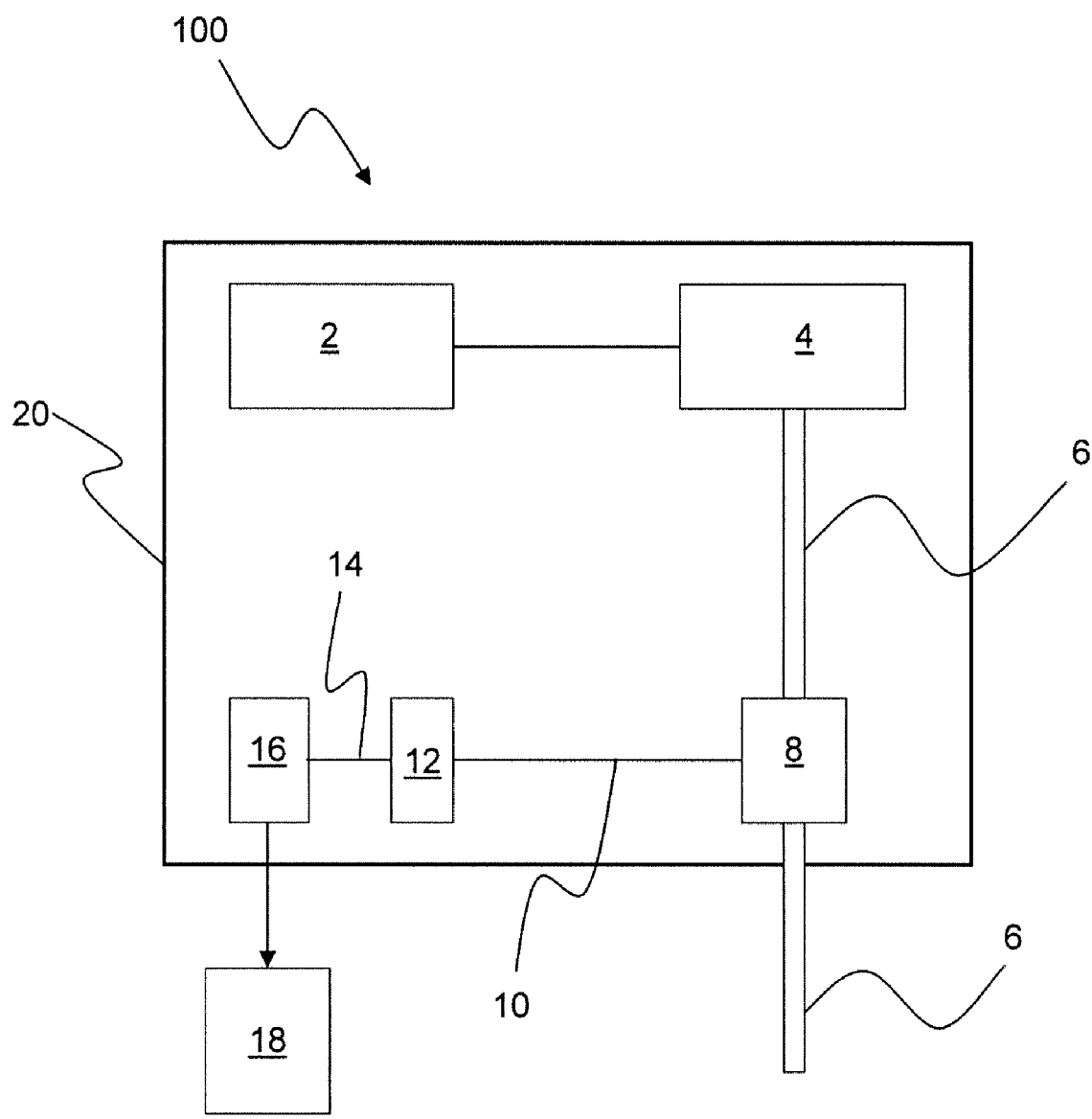
FIG. 5 is a schematic representation of a portion of a portable device as described herein.

In accordance with the present technology, one or more optical fibers may be utilized as a portion of a portable sensing device, one embodiment of which is schematically illustrated in FIG. 5. As may be seen according to this particular embodiment, several of the components corresponding to device 100 may be housed within an enclosure 20.

Enclosure 20 may be, for example, a molded plastic enclosure of a size so as to be easily carried by or attached to a wearer. For instance, enclosure 20 may include clips, loops, or the like so as to be attachable to a patient's clothing or body. In one embodiment, enclosure 20 may include an adhesive surface, and may be adhered directly to a patient's skin. In general, enclosure 20 may be relatively small, for instance less than about 10 cm by about 8 cm by about 5 cm, so as to be inconspicuously carried by a patient and so as to avoid impedance of a patient's motion. Enclosure 20 may completely enclose the components contained therein, or may partially enclose the components contained therein. For example, enclosure 20 may include an access port (not shown) that may provide access to the interior of enclosure 20. In one embodiment, an access port may be covered with a removable cover, as is known in the art.

A first component as may be held within enclosure 20 is power supply 2 that may be configured in one embodiment to supply power to an excitation source 4 as well as other of the operational components as will be later described. In an exemplary configuration, power supply 2 may correspond to a battery, however those of ordinary skill in the art will appreciate that other power supplies may be used including those that may be coupled to an external alternating current (AC) supply so that the enclosed power supply may include those components necessary to convert such external supply to a suitable source for the remaining components requiring a power source.

As previously noted, power supply 2 may be configured in one embodiment to supply power to excitation source 4. In particular, an excitation source 4 may be included within enclosure 20 in those embodiments in which the optical cable 6 includes thereon a FRET pair, the donor of which requires excitation from an external source. In other embodiments, however, for instance in those embodiments in which donor molecule excitation is provided according to a luciferase/luciferin interaction, an excitation source 4 need not be included in enclosure 20.

In the illustrated exemplary configuration, excitation source 4 may correspond to a light emitting diode (LED), however, again, such source may vary and may include, but is not limited to, laser diodes and incandescent light sources. Excitation source 4 may correspond to a white light source, a non-white multi-wavelength source, or a single wavelength source, as desired or required. In a preferred exemplary configuration, an LED may be selected due to the low power consumption of such sources. The wavelength of the excitation energy supplied by excitation source 4 may be of any suitable wavelength, from infrared (IR) to ultraviolet (UV). In general, the preferred excitation energy wavelength may depend upon the specific design of the RET pairs. For instance, in those embodiments in which a single FRET donor molecule is utilized, an excitation source 4 may provide a single excitation wavelength. In other embodiments, however, for instance when a plurality of different donor molecules are included on the same or different fibers, and the different donor molecules respond to different excitation wavelengths, an excitation source may provide multiple wavelengths, either through combination of signals from a plurality of single wavelength sources or through a single, incoherent source, as desired.

Excitation energy source 4 is optically coupled to an optical fiber 6 as illustrated. Optical fiber 6 is configured to extend externally from enclosure 20 to the field of inquiry, e.g., within a surgical site or other wound. It should be appreciated that although optical fiber 6 is illustrated in FIG. 4 as including only a single optical fiber, such is not a specific limitation of the present disclosure as such devices may, in fact, include optical cables that include multiple fibers in alternate embodiments, and as discussed above. Those of ordinary skill in the art will appreciate that a single excitation energy source may be optically coupled to a plurality of optical fibers through utilization of suitable beam splitters, mirrors, and so forth.

Moreover, as discussed previously, plural excitation energy sources may be used. In such a configuration, each excitation source may be optically coupled to one or more optical fibers such that multiple excitation wavelengths may be delivered to the field of enquiry.

Housed within enclosure 20 is an optical detector 8 coupled to optical fiber 6. Optical detector 8 may correspond to a photodiode, a photoresistor, or the like. Optical detector 8 may include optical filters, beam splitters, and so forth that may remove background light and reduce the total input optical signal at the detector 8 to one or more diagnostically relevant emission peaks. Optical detector 8 may produce a signal proportional to targeted emission peaks and couple such signal to line 10 for transmission to signal processor 12.

Signal processor 12 may include a microprocessor configured to evaluate the strength or other characteristics of the output signal received over line 10 to, e.g., detect which specific enzyme is present in the field of enquiry and to produce a detection signal that may be coupled to line 14 for passage to a signaling device 16. Accordingly, if the detection signal reaches a predetermined threshold value, corresponding to a positive determination of the target enzyme and hence the pathogen, a detectable signal may be initiated at signaling device 16. In an exemplary configuration, a detectable signal may initiate a visible or audible signal that may be detected by the wearer within or at the surface of the enclosure 20 by way of signaling device 16. For instance, a visible signal may optionally include utilization of a liquid crystal diode (LCD) device, or an equivalent thereof, that may provide the signal as a readable output. For example, a visual signal may be provided at a surface of the device as an instruction such as, for instance, "CALL YOUR DOCTOR", "VISIT HOSPITAL," or the like.

In addition to or alternative to a visual and/or audible signal at the enclosure 20 itself, signaling device 16 may include a transmitter portion that, upon initiation of the detectable signal, may transmit an electromagnetic signal to receiver 18. Receiver 18 may be remote from the signaling device 16. For instance, receiver 18 may be on the wearer's body at a distance from the signaling device 16, at a location apart from the wearer's body that may be conveniently chosen by the wearer, e.g., within the wearer's home, office, or the like, or may be at a monitoring facility, for instance at a medical facility, such that appropriate medical personal may be quickly informed of the change in status of the patient's site of inquiry. In alternative embodiments, the detectable signal may be transmitted to multiple receivers, so as to inform both the wearer and others (e.g., medical personnel) of the change in status of a site. Transmission of a signal to a remote site may be carried out with a radio frequency transmission scheme or with any other wireless-type transmission scheme, as is generally known in the art. For instance, a wireless telephone or internet communications scheme could be utilized to transmit a signal to a remote location according to known methods.

Wireless transmission systems as may be utilized in conjunction with disclosed devices and methods may include, for example, components and systems as disclosed in U.S. Pat. No. 6,289,238 to Besson, et al., U.S. Pat. No. 6,441,747 to Khair, et al., U.S. Pat. No. 6,802,811 to Slepian, U.S. Pat. No. 6,659,947 to Carter, et al., and U.S. Pat. No. 7,294,105 to Islam, all of which are incorporated in their entirety by reference.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for detecting the presence or amount of a pathogen that is a source of a hospital acquired infection comprising:

locating an optical fiber in an environment, the optical fiber having directly or indirectly attached thereto a first group of molecules at a site that is within the evanescent field of the core of the optical fiber, the first group of molecules including an acceptor molecule, one of the molecules of the group being attached to the optical fiber with a first tether, the first tether comprising a substrate cleavable by an enzyme that is expressed by the pathogen;

retaining the optical fiber in the environment such that enzyme present in the environment will cleave the substrate;

transmitting an excitation signal to the site via the optical fiber, the excitation signal comprising an excitation wavelength specific for a donor molecule;

transmitting an optically detectable emission signal from the site following any cleaving of the substrate by action of the enzyme; and determining the presence or amount of the pathogen in the environment based on the detectable emission signal.

2. The method according to claim 1, wherein the group of molecules includes the donor molecule.

3. The method according to claim 2, wherein the acceptor molecule is attached to the optical fiber with the first tether.

4. The method according to claim 1, further comprising degrading a matrix, the matrix encapsulating the group of molecules.

5. The method according to claim 4, wherein the matrix is a polymeric matrix.

6. The method according to claim 1, wherein the environment is an in vivo environment.

7. The method according to claim 1, wherein the environment is a surgical site.

8. The method according to claim 1, further comprising converting the optically detectable emission signal to an electromagnetic signal.

9. The method according to claim 8, further comprising transmitting the electromagnetic signal to a receiver.

10. The method according to claim 9, wherein the electromagnetic signal is transmitted to the receiver according to a wireless transmission system.

11. The method according to claim 1, wherein the optical fiber is a first fiber in a multi-fiber cable, the cable further comprising a second optical fiber.

12. The method according to claim 11, the second optical fiber having attached thereto a second group of molecules at a site that is within the evanescent field of the core of the second optical fiber, the second group of molecules including a second acceptor molecule, one of the second group of molecules being attached to the second optical fiber with a second tether, the second tether comprising a substrate for an enzyme that is expressed by a pathogen that is a source of hospital acquired infection, the method further comprising transmitting a second excitation signal to the second group of molecules via the second optical fiber.

13. The method according to claim 12, wherein the first excitation signal is transmitted via the first optical fiber and the second excitation signal is transmitted via second optical fiber sequentially.

14. The method according to claim 1, the group of molecules further comprising a second enzyme and a molecular cofactor, wherein one of the second enzyme and the molecular cofactor is attached to the optical fiber with the first tether, the second enzyme and the molecular cofactor interacting following cleavage of the substrate, wherein interaction between the molecular cofactor and the second enzyme generates a donor molecule at an excited state.

15. A portable device for detecting the presence or amount of a pathogen that is a source of a hospital acquired infection comprising:
a portable enclosure containing a power source, an excitation source, an optical detector, a signal processor, and a signaling device for emitting a signal upon detection of an enzyme that is expressed by the pathogen;
a connecting device for attaching the enclosure to the clothing or body of a wearer;
a fiber optic cable for inserting into an environment, the fiber optic cable being in optical communication with the optical detector, the fiber optic cable extending for a length exterior to the enclosure, the fiber optic cable comprising an optical fiber; and
a group of molecules directly or indirectly attached to the optical fiber at a site that is within the evanescent field of the core of the optical fiber, the group of molecules including an acceptor molecule, wherein one of the group of molecules is attached to the optical fiber with a tether comprising a substrate cleavable by an enzyme that is expressed by the pathogen.

16. The device of claim 15, the group of molecules further comprising a donor molecule.

17. The device of claim 15, the device further comprising a degradable matrix encapsulating the group of molecules.

18. The device of claim 15, wherein the fiber optic cable contains a plurality of optical fibers.

19. The device of claim 15, the portable enclosure further comprising a transmitter in electrical communication with the signaling device, wherein the signal emitted from the signaling device is subsequently transmitted from the transmitter.

20. The device of claim 19, further comprising a receiver, wherein the transmitter is in wireless communication with the receiver.

21. The device of claim 15, wherein the connecting device is for connecting the enclosure to a piece of clothing.

22. The device of claim 15, wherein the connecting device is for connecting the enclosure to a wearer's skin.

23. The device of claim 15, wherein the group of molecules is directly attached to a particle.

24. The device of claim 15, further comprising a semipermeable barrier surrounding at least a portion of the fiber optic cable.

25. The device of claim 15, the group of molecules further comprising a second enzyme and a molecular cofactor.

26. The device of claim 25, wherein the second enzyme is luciferase and the molecular cofactor is luciferin.

* * * * *

UNITED STATES PATENT AND TRADEMARK OFFICE
CERTIFICATE OF CORRECTION

PATENT NO. : 8,180,421 B2
APPLICATION NO. : 11/954848
DATED : May 15, 2012
INVENTOR(S) : Erica M. Phillips et al.

It is certified that error appears in the above-identified patent and that said Letters Patent is hereby corrected as shown below:

Title page 2, item (56) References Cited, Foreign Patent Documents "WO2006086878" should read --WO2006086578--

Signed and Sealed this
Twenty-fourth Day of September, 2013

Teresa Stanek Rea
*Deputy Director of the United States Patent and Trademark Office*